United States Patent
Chang

(10) Patent No.: US 8,709,490 B2
(45) Date of Patent: Apr. 29, 2014

(54) ACTIVE PELLET WITHOUT CHEMICAL ADDITIVES

(75) Inventor: Chao-Hsiang Chang, New Taipei (TW)

(73) Assignees: bio-Trend Pharmaceutical Co., Ltd, Taipei (TW); Decken Biotech, Inc, Taichung (TW)

( * ) Notice: Subject to any disclaimer, the term of this patent is extended or adjusted under 35 U.S.C. 154(b) by 0 days.

(21) Appl. No.: 13/571,367

(22) Filed: Aug. 10, 2012

(65) Prior Publication Data

US 2013/0039988 A1     Feb. 14, 2013

(30) Foreign Application Priority Data

Aug. 10, 2011    (TW) .............................. 100214828 U

(51) Int. Cl.
*A61K 9/50*         (2006.01)
*A61K 9/14*         (2006.01)

(52) U.S. Cl.
USPC ........................................... 424/499; 424/489

(58) Field of Classification Search
None
See application file for complete search history.

(56) References Cited

FOREIGN PATENT DOCUMENTS

EP        2291233 A1 * 5/2011

OTHER PUBLICATIONS

"Using Cellulose Ethers for Controlled Release of Drugs in Hydrophilic Matrix Systems", Dow Chemical Company, Jul. 2000.*

* cited by examiner

*Primary Examiner* — Carlos Azpuru
(74) *Attorney, Agent, or Firm* — CKC & Partners Co., Ltd.

(57) ABSTRACT

Disclosed herein is an active pellet. The active pellet includes a body and interspaces. The body includes an active ingredient ranging from 50 to 100 wt %, free of chemical additives.

2 Claims, 4 Drawing Sheets

ACTIVE PELLET WITHOUT CHEMICAL ADDITIVES

RELATED APPLICATIONS

This application claims priority to Taiwan Application Serial Number 100214828, filed Aug. 10, 2011, which is herein incorporated by reference.

BACKGROUND

1. Technical Field

The present disclosure relates to an active pellet without chemical additives.

2. Description of Related Art

A liquid lamination process, a powder lamination process or extrusion with spheroization can be utilized to form typical pellets. The liquid lamination process includes the steps of dissolving an active ingredient in a solvent and adding a polymer binder, adhering viscous fluid over a core by a spray-drying process, and forming the pellets of multiplayer by a lamination process. The powder lamination process includes spraying the polymer binder on a powder, and then laminating multi-layers to form the pellets. The polymer binder is also applied during performing extrusion with spheroization in favor of shaping. However, the polymer binder belongs to a artificial chemical additive, which has no benefit to human bodies.

A typical active powder is formed by extracting and drying an active ingredient. Nevertheless, the active powder has various sizes, and the diameter thereof is no more than about 100 μm. The shape of the powder may be in a form of needles, flakes, irregular-shaped objects or round particles. The active powder is easy to absorb moisture to become viscous and generate mucus, and thus it is not easy to flow. If the powder needs to employ further processing, lubricant (e.g., talc, magnesium stearate, and etc.) is needed to add thereinto to facilitate the flowing. The lubricant is utilized to cover the surface of the active powder to make it smooth to flow. However, the lubricant not only affects disintegration and solubility of the active ingredient in the formulation but also cause burden to the human body.

In addition, to improve the characteristics of the formulation, other to chemical additives may be added. As an example, preservatives are added to enhance stability. Flavoring agent, spices or artificial colors are used to change flavor and appearance. Also, a disintegrating agent can be added to adjust disintegration rate.

From the above, chemical additives may be used during the process for manufacturing traditional pellets or formulations; also, other chemical additives may be added to improve the characteristics of the formulation. However, long-term taking the formulation containing chemical additives may have adverse effects to the human body.

Therefore, there is a need for an active pellet free of any artificial chemical additive but still with good workability, such that it does not require any chemical additives during formulation.

SUMMARY

The following presents a summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

An aspect of the present disclosure provides an active pellet without chemical additives, which includes a body and interspaces. The body includes an active ingredient ranging from 50 to 100 wt %, free of chemical additives.

In one embodiment of the present disclosure, the body further includes less than or equal to 40 wt % of a natural diluent, which is a material selected from the group consisting of lactose, sucrose, glucose, calcium carbonate, calcium phosphate, starch, microcrystalline cellulose, ginger, turmeric, pepper, garlic, astragalus, bamboo leaves, mangosteen shell, rambutan peel, yam, tea, orange peel, sweet potato peel, potato peel, dried bagasse powder and a combination thereof.

In one embodiment of the present disclosure, the body further includes less than or equal to 10 wt % of a binder, which is a material selected from the group consisting of sugar, starch, gum arabic, cellulose derivatives and a combination thereof.

In one embodiment of the present disclosure, the body has a particle size ranging from 100 to 1800 μm.

In one embodiment of the present disclosure, the interspaces are in a form of honeycomb holes or textures.

In one embodiment of the present disclosure, each of the hone comb holes or each of the textures has a width ranging from 0.1 to 100 μm.

in one embodiment of the present disclosure, the body includes a fine powder having a particle size ranging from 20 to 160 μm.

In one embodiment of the present disclosure, the active pellet further includes liquid disposed in the interspaces.

In one embodiment of the present disclosure, the active pellet further includes a covered layer covering the surface of the body.

Another aspect of the present disclosure provides a tablet composed of the active pellets mentioned above.

Compared to the prior art, the embodiments according to the present disclosure have advantages as follows.

1. According to the embodiment of the present disclosure, the active pellet does not contain chemical additives, such that can reduce a pill taker's mental stress and effect of physical health.

2. According to the embodiment of the present disclosure, the active pellets have higher density and better size uniformity than typical granules or powders, and thus have controlled-release or delayed-release effects.

3. According to the embodiment of the present disclosure, the ball-like body has a large particle size and thus exhibits good flow ability, such that lubricant is not used in further processing for manufacturing formulation such as capsules or tablets.

4. According to the embodiments of the present disclosure, the body can be a viscous substance, which is suitable for further processing.

5. According to the embodiments of the present disclosure, the active pellet has interspaces and thus exhibits better disintegration.

BRIEF DESCRIPTION OF THE DRAWINGS

The disclosure may be more fully understood by reading the following detailed description of the embodiment, with reference made to the accompanying drawings as follows.

DETAILED DESCRIPTION

Figure 1A:
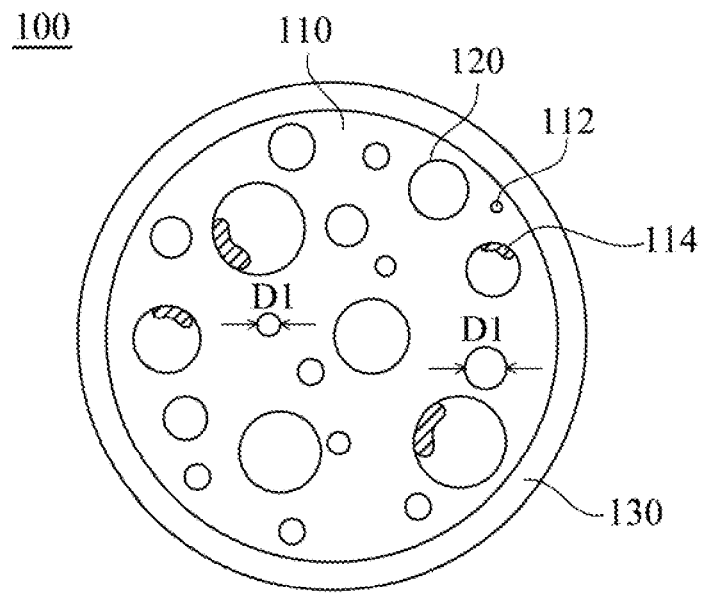
FIGS. 1A to 1B are cross-sectional views schematically illustrating active pellets according to embodiments of the present disclosure.

The present invention is described by the following specific embodiments. Those with ordinary skill in the arts can readily understand the other advantages and functions of the present invention after reading the invention of this specification. The present invention can also be implemented with different embodiments. Various details described in this specification can be modified based on different viewpoints and applications without departing from the scope of the present invention.

As used herein, the singular forms "a," "an" and "the" include plural referents unless the context clearly dictates otherwise. Therefore, reference to, for example, a metal wire includes aspects having two or more such metal wires, unless the context clearly indicates otherwise.

Reference will now be made in detail to the embodiments of the present invention, examples of which are illustrated in the accompanying drawings. Wherever possible, the same reference numbers are used in the drawings and the description to refer to the same or like parts.

Figure 1B:
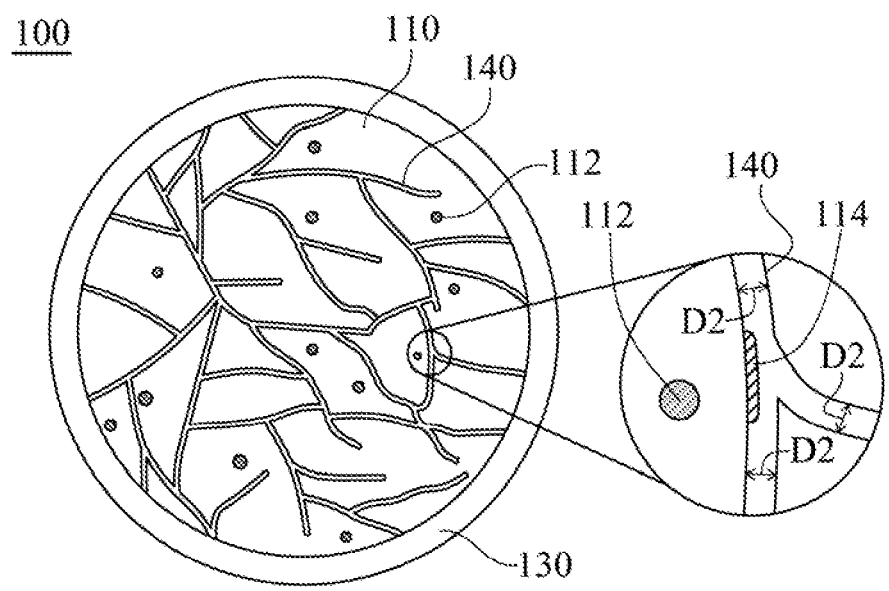

FIGS. 1A to 1B are cross-sectional views schematically illustrating active pellets 100 according to embodiments of the present disclosure. The active pellet 100 includes a body 110 and interspaces disposed therein. In one embodiment, the interspaces are in a form of honeycomb holes 120, as shown in FIG. 1A. In another embodiment, the interspaces are in a form of textures 140, as shown in FIG. 1B.

The active pellet 100 can be formed by extrusion with spheronization. During performing the extrusion process, process conditions such as a water ratio, the diameter of apertures of a mold, extrusion stress and a rate of extrusion can be controlled, and thus there is no need to add any chemical additive.

In one embodiment, the body 110 is ball-like in shape. The body 110 has a particle size ranging from 100 to 1800 μm, which can be adjusted in accordance with applications demand. For instance, the particle size of the active pellet 100 can be designed according to disintegration and a desired rate of release. Further, compared to a typical active powder, the body 110 has higher density and better size uniformity, and thus has good controlled-release effect.

The ball-like body 110 refers to the body 110 has a shape in a form of a sphere, an ellipsoid, or close to a sphere or an ellipsoid. Because the ball-like body 110 is easy to roil and not vulnerable to moisture to further produce mucus, it can exhibit better flow ability during further processing without adding lubricant.

In one embodiment, the body 110 includes a fine powder 112; that is, the body 110 includes a continuous or a non-continuous structure. The fine powder 112 can be obtained by extraction, drying and crush process in sequence. The fine powder 112 has a particle size ranging from 20 to 160 μm, and it is ball-like in shape or has a fixed shape or a non-fixed shape.

In one embodiment, the honeycomb hole 120 has a width D1 ranging from about 0.1 to 100 μm, as shown in FIG. 1A.

In another embodiment, the texture 140 has a width D2 ranging from about 0.1 to 100 μm, as shown in FIG. 1B. The textures 140 have a shape in a form of ice cracks typically having a linear shape; in other words, the textures 140 have a shape like the generated textures when ice cracks. The textures 140 are connected to each other. The active pellet 100 exhibits good disintegration due to the interspaces therein. The interspaces of the active pellet 100 can be formed by internal stress generated by extrusion and spheronization.

In one embodiment, the active pellet 100 further includes liquid 114 in the interspaces. As shown in FIG. 1A and FIG. 1B, the liquid 114 is disposed in the honeycomb holes 120 or the textures 140. The liquid can be a liquid active ingredient, such as an oil ingredient exhibiting a pharmacological effect.

The covered layer 130 is disposed on the surface of the body 110. The covered layer 130 is utilized to protect the body 110, elevate stability of the active pellet 100 and control a rate of release of an active ingredient. The covered layer 130 can be in a form of a sugarcoated layer or a film-coated layer.

Moreover, the active pellet 100 can be further processed to form various formulations, such as a capsule 200, a tablet 300 or a granule 400.

Figure 2:
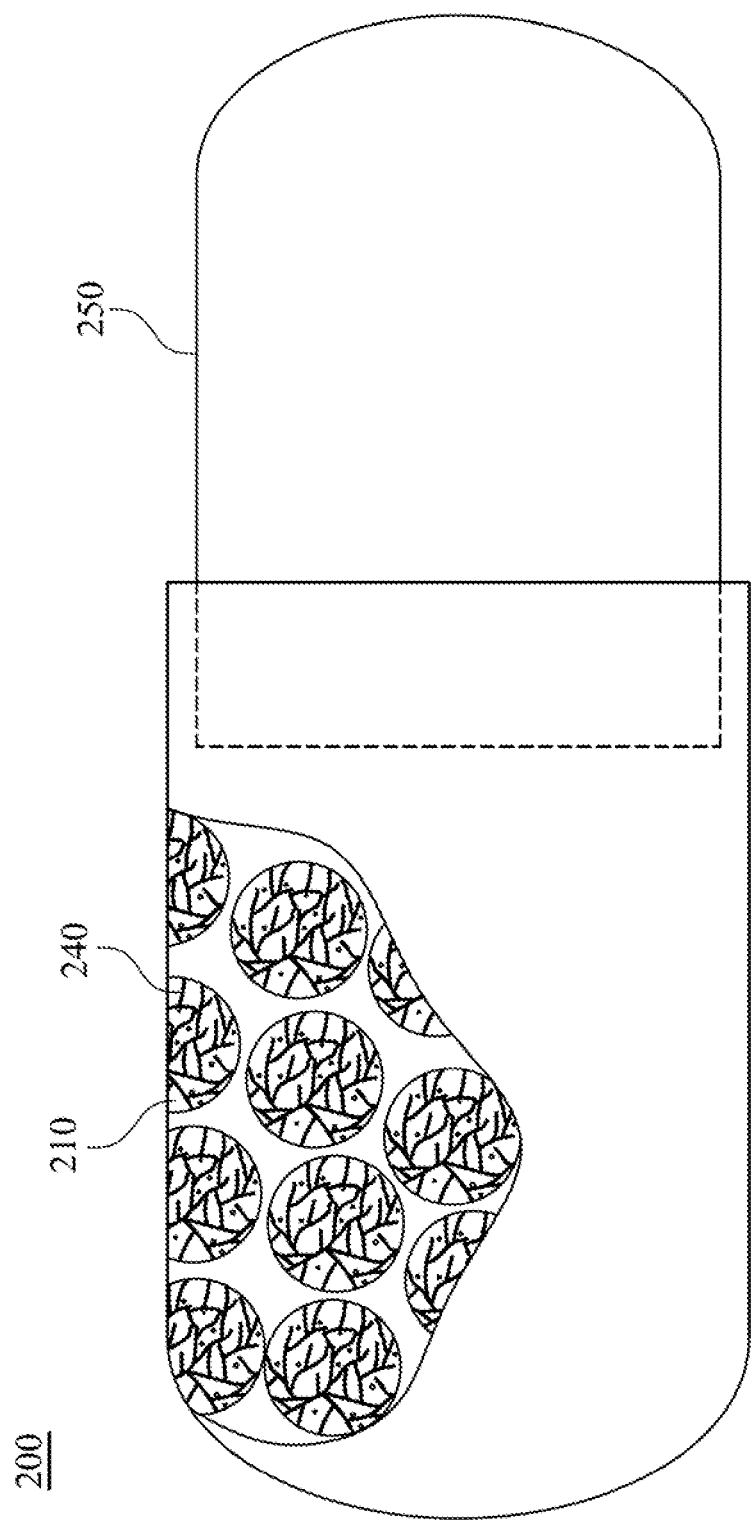
FIG. 2 is a cross-sectional view schematically illustrating a capsule according to one embodiment of the present disclosure.

FIG. 2 is a cross-sectional view schematically illustrating a capsule according to one embodiment of the present disclosure. The capsule 200 includes active pellets 210 and a capsule shell 250. In the embodiments, the active pellet 210 has textures 240. Since the ball-like body of the active pellet 210 is not vulnerable to moisture to further produce mucus, it can be filled in the capsule shell 250 without adding lubricant.

Figure 3:
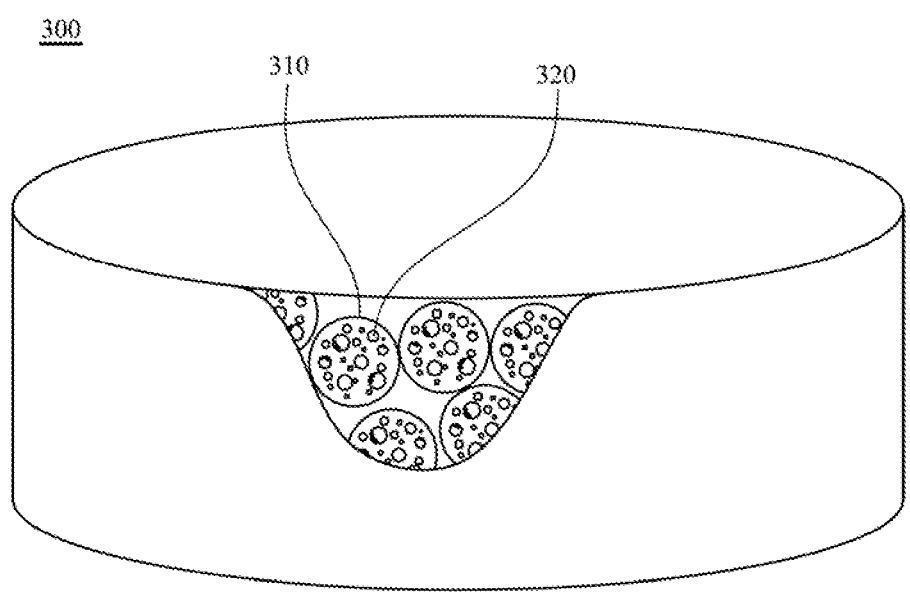
FIG. 3 is a cross-sectional view schematically illustrating a tablet according to one embodiment of the present disclosure.

FIG. 3 is a cross-sectional view schematically illustrating a tablet according to one embodiment of the present disclosure. In the embodiment, the tablet 300 is manufactured by a wet granulation process. First, the active pellets 310 are mixed with water or ethanol and then dried, and forming the tablet 300 by a tablet machine. Since the active pellets 310 have good compression property, the manufacturing process is employed without adding excipient.

Figure 4:
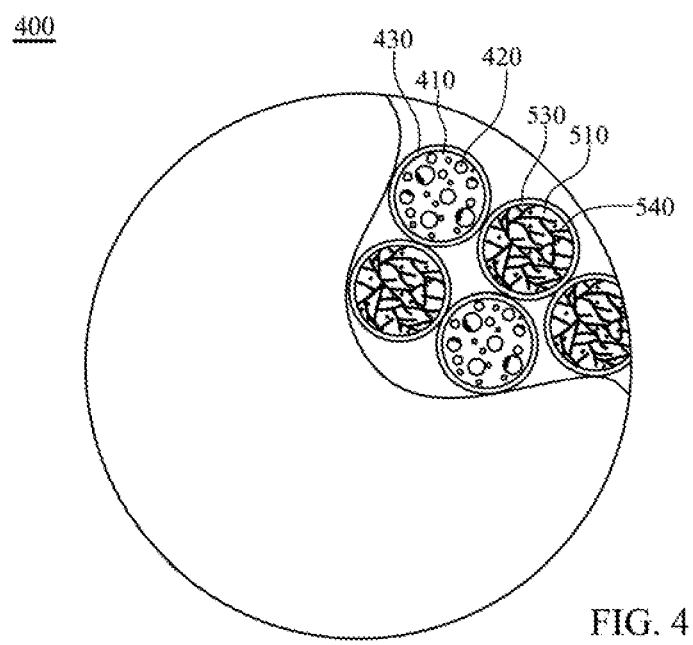
FIG. 4 is a cross-sectional view schematically illustrating a granule according to one embodiment of the present disclosure.

FIG. 4 is a cross-sectional view schematically illustrating a granule according to one embodiment of the present disclosure. In the embodiment, the granule 400 includes the active pellets 410 having the honeycomb holes 420 and the active pellets 510 having the textures 540. In addition, two active pellets 410, 510 also include covered layers 430, 530. The active pellets 410, 510 can be processed by extrusion or a finishing process to form elongated granules or ball-like granules 400 having a diameter ranging from 300 to 1800 μm.

As mentioned above, the processes for manufacturing the capsule 200, the tablet 300 and the granule 400 are employed without adding chemical additives. Also, compared to typical granules or powders, the formulations mentioned above have better delayed-release effect, storage stability and biological stability.

Composition of Body of Active Pellet

In one embodiment, the composition of the body 110 is 100% active ingredient, free of chemical additives. The chemical additives refer to the substances synthesized by chemical processes and having certain functions. The chemical additives can be excipient, binders, disintegrating agents, diluents, glidants, lubricants, flavoring agents, emulsifiers, preservatives, spices or artificial colors.

The active ingredients can be applied in the fields of food or drugs. The active ingredients can be divided into active substances or adjuvant-active substances in accordance with activity thereof. The active substance can be organic acids, fatty acids, polypeptide, protein, probiotics, fungi, algae, alkaloids, flavonoids, minerals or chemical compounds. The adjuvant active substance may be polysaccharide, sugars or cellulose.

The organic acids may be citric acid, malic acid, lactic acid, corn fermentation product, fruit fermentation product or other organic acids that can be added in food.

The fatty acids can be unsaturated fatty acids having carbon atoms of one of the carbon chains less than 50, such as Omega3, Omega6, Omega9, lecithin or phosphoric acid serine.

The polypeptide or protein may be the polypeptide or protein exhibiting physiological regulation.

The probiotics can be the genus *Lactobacillus*, the genus *Bifidobacterium*, *Bacillus* spp, *Bacillus subtilis*, *Streptococcus, Enterococcus* or *Saccharomyces*.

The fungi can be fungal mycelium or fungal fruiting bodies applied to food or drugs, *Ascomycetes* fungi or *Basidiomycetes* fungi. As an example, the fungi may be *Antrodia camphorata, Cordyceps sinensis, Ganoderma lucidum, Cordyceps Militaris*, honeycomb Chi or split fold bacteria.

The algae can be applied to food or drugs, such as cyanobacteria, grape algae, green algae, red algae, nuclear algae, Karber hidden dinoflagellates, Medusa algae, purple algae or Aphanizomenon algae.

The alkaloids may be the alkaloids that extracted from plants, animals or fungal, or that may be applied to food additives. The alkaloids can be piperine, trigonelline, theophylline, caffeine, resveratrol, serotonin, ergot and derivatives thereof, carnitine or choline.

The flavonoids may be the flavonoids that extracted from fruits, vegetables, tea, wine, seeds, roots of plants, or that may be applied to food additives. For example, the flavonoids can be flavonoids rutin, hesperidin, quercetin, green tea polyphenols, red wine polyphenols or olive polyphenol.

The minerals can be edible or applied to food additives, such as sodium, calcium, chromium salts, zinc salts, iron salts, magnesium salts or selenium salts.

The cellulose may be extracted from ginger, turmeric, pepper, garlic, Astragalus, bamboo leaves, mangosteen shell, orange peel, rambutan peel, yam or tea leaves.

In one embodiment, the active ingredient is a natural fiber, which can dilute and adhere, and thus the manufacturing process can be performed without any diluent and binder.

In another embodiment, the body 110 of the active pellet 100 includes an active ingredient and adjuvant substances including a natural diluent, a natural binder and a natural wetting agent.

The natural diluent is utilized to increase weight and volume of the body to be easily shaped and divided, and it does not have any pharmacological effect. The natural diluent such as lactose, sucrose, glucose, calcium carbonate, calcium phosphate, starch, microcrystalline cellulose, ginger, turmeric, orange peel, sweet potato peel, potato peel, dried bagasse powder or a combination thereof.

The natural binder is used to aggregate or compress non-sticky substances or slightly viscous substances to form viscous particles, powders or liquid, and it does not exhibit any active pharmacological effect. The natural binder can be sugars, starch, gum arabic, cellulose derivatives or a combination thereof.

The natural wetting agent is utilized to wet the active ingredient and the adjuvant substances to achieve enough viscosity, thus to easily form pellets. The wet materials (refers to the proposed processing substances, in this case refers to the active ingredient plus the adjuvant substances) contacting the wetting agent would aggregate to form a soft material to further form pellets. Nevertheless, the wetting agent does not have high viscosity. The wetting agent is used during the process but not existed in the final product. In one embodiment, the wetting agent is water.

In the embodiments, the active ingredient of the body has a weight ratio ranging from 50 to 100%, the natural diluent having a weight ratio ranging from 0 to 40%, and the binder has a weight ratio ranging from 0 to 10%.

Method for Manufacturing Active Pellet

The active pellets can be manufactured by different processes. In accordance with mechanisms, the processes can be a powder lamination process, a liquid lamination process, extrusion with spheroization or a combination thereof. In embodiments, extrusion with spheroization is employed as a main process or the only process.

First, a combination of materials is selected according to the properties of the materials. In one embodiment, natural fiber exhibiting a pharmacological activity is selected as the active ingredient. Water is added to the natural fiber to form a soft material having enough viscosity to be shaped. Extrusion with spheroization and a drying process are sequentially performed to form ball-like active pellets exhibiting enough structural strength. In the embodiment, since the active ingredient (i.e., the natural fiber) can dilute and adhere to other substances, there is no need for any diluent and binder during all the process.

In another embodiment, since the active ingredient exhibiting inadequate viscosity is selected, other substances such as a natural diluent and/or a binder should be added.

Subsequently, the selected substances are pre-treated. In one embodiment, the substances are processed to form a product having honeycomb holes. For instance, water is added to the natural diluent (e.g., ginger fiber) and then mixed and stirred, if necessary, a binder is added. After stirring, a loose structure having voids is formed. The active ingredient is then added to the loose structure to form the product having the honeycomb holes.

In one embodiment, a product having textures is formed. For instance, water, the natural diluent (e.g., ginger fiber) and the active ingredient are mixed and stirred, if necessary, a binder is added. An extrusion process is then performed to form the elongated particles. The cycling times of the extrusion process are not limited, which can be determined according to the structural strength of pellets.

The extruder may be a single-screw extruder or a twin-screw extruder. A circular orifice plate is set at the front-end of the extruder, or an arc orifice plate is set on both sides thereof. When the screw moves forward and squeezes both sides, the material is extruded from the round holes (i.e., pressure vent port) of the orifice plate.

In one embodiment, when the screw pushes the material, the pressure near the orifice plate is in a range of 2000 to 30000 psi for forming elongated particles. The pressure is related to the diameter of the round hole and an opening ratio of the orifice plate. The density of the extruded particles is higher when the pressure is higher to decrease taking amounts of the natural diluent and the binder.

In one embodiment, the diameter of the hole is in a range of 0.2 to 1.8 mm. While the diameter of the hole is smaller, the pressure is higher to decrease taking amounts of the natural diluent and the binder.

Next, a centrifugal turntable and an additional machine are used to perform a spheronization process to cut the elongated particles. During the spheronization process, particles collide with each other or with the inner wall of the machine to thereby form ball-like pellets. Further, controlling a rate of spheronization, process time and using a cutting plate of the additional machine can improve the appearance of the active pellets.

Finally, a drying process is performed to form the active pellets having textures.

The active pellets can be applied to physiological or pharmacological uses. As an example, the active pellets can be applied to regulate physiological changes caused by physiological disorders or indications, such as sleep disorders, including insomnia, light sleep, anxiety, and etc.; environmental pollution, including heavy metals, environmental hormones, pesticides, intake or absorption of yellow aflatoxin, and etc.; gastrointestinal disorders, including constipation, flatulence, diarrhea, and etc.; metabolic syndrome, including obesity, high cholesterol, fatty liver, diabetes, and etc.

Embodiments

Embodiment 1

The compositions of Comparative Example 1, Comparative Example 2, Example 1 and Example 2 are listed in Table 1. In Comparative Example 1, the active ingredient and the diluent (total 500 g) were uniformly mixed, and 150 ml hydroxypropyl methyl cellulose (HPMC) aqueous solution (5%) was then added. Next, elongated particles are formed by using a single-screw extruder (hole size 1.0 mm), and then spheronized by using a centrifugal turntable at 500 rpm for 30 seconds. The particles formed after the spheronization process was then dried at 60° C. for 3 hours to obtain active pellets.

The active pellets of Comparative Example 2, Example 1 and Example 2 were fabricated by the same processes mentioned above with different compositions.

TABLE 1

|  | Active Ingredient | Diluent | Binder |
| --- | --- | --- | --- |
| Comparative Example 1 | Vitamin C powder 90% | microcrystalline cellulose 10% | HPMC aqueous solution (5%) |
| Comparative Example 2 | Vitamin C powder 50% | lactose 50% | HPMC aqueous solution (5%) |
| Example 1 | Vitamin C powder 75% | microcrystalline cellulose 25% | HPMC aqueous solution (5%) |
| Example 2 | Vitamin C powder 85% | ginger fiber 15% | HPMC aqueous solution (5%) |

The amount of the diluent of Comparative Example 1 was low. Although the composition of Comparative Example 1 was capable of performing to extrusion and spheronization, the formed active pellets had a relatively loose structure and exhibit lower density. When filling the active pellets into a capsule shell (i.e., automatic filling process), the loss ratio was up to about 20% since the active pellets easily turned into fine powders. No. 0 capsule had an average filling amount of about 400 mg (the theoretical value is 500 mg), which meant the active pellets had a loose structure and were not suitable for further processing to manufacture capsules.

The amount of the diluent of Comparative Example 2 was large. Although the composition of Comparative Example 2 was capable of performing an extrusion process, the formability is not good. Consequently, lactose was not a suitable diluent. It is because lactose may absorb moisture and then dissolve itself, such that the composition is incapable of forming a stable structure.

In Example 1 and Example 2, the yields of sorting pellets (the pellets are extruded from a 1.0 mm orifice plate, and the diameters of pellets are in a range of 0.81 to 0.90 mm) are up to 90%. No. 0 capsule has an average filling amount of about 500 mg, and the filling loss (i.e., loss ratio) is lower than 5%, which means the active pellets have suitable flow ability and structural rigidity.

Further, the ginger fiber (i.e., ginger powder obtained from ginger juice processed by squeezing, drying and crush processes) has suitable formability compared to a typical diluent (e.g., microcrystalline cellulose). Further, the ginger fiber belongs to a natural product, which is not formed through artificially chemical processes.

Embodiment 2

Both the compositions and the conditions of the extrusion process of Examples 1-4 are listed in Table 2. The active ingredient and the diluent (total 500 g) were uniformly mixed, and 150 ml binder (respectively are 5% HPMC aqueous solution, 1% HPMC aqueous solution and water) was then added therein. Subsequently, elongated particles were extruded by using a single-screw extruder (hole size 1.0 mm or 0.4 mm), and then spheronized by using a centrifugal turntable at 500 rpm for 30 seconds. The particles formed after the spheronization process Was then dried at 60° C. for hours to obtain active pellets.

TABLE 2

|  | Diameter of Hole (mm) | Density of Hole (%) | Active Ingredient | Diluent | Binder |
| --- | --- | --- | --- | --- | --- |
| Example 1 | 1.0 | 20 | Vitamin C powder 75% | microcrystalline cellulose 25% | HPMC aqueous solution (5%) |
| Example 2 | 1.0 | 20 | Vitamin C powder 85% | ginger fiber 15% | HPMC aqueous solution (5%) |
| Example 3 | 0.4 | 3 | Vitamin C powder 75% | microcrystalline cellulose 25% | HPMC aqueous solution (1%) |
| Example 4 | 0.4 | 3 | Vitamin C powder 85% | ginger fiber 15% | water |

In Example 3 and Example 4, the pellets (extruded from a 0.4 mm orifice plate and having diameters in a range of 0.3 to 0.4 mm) were ball-like in shape and exhibited good size uniformity. No. 0 capsule had an average filling amount of about 500 mg, and the filling loss (i.e., loss ratio) is lower than 5%, which means the active pellets had suitable flow ability and structural rigidity. In other words, using the orifice plate having smaller holes and lower density of holes could form suitable active pellets without adding a binder or under a composition with low viscosity.

Embodiment 3

Both the compositions and conditions of the pre-treated process of Examples 5 to 8 are listed in Table 3. The active ingredient (powders or active pellets), the diluent and the binder had a total weight of 500 g. The pre-treated process and extrusion with spheronization process were performed in sequence.

TABLE 3

|  | Active Ingredient | Diluent | Binder | Pre-treated Process |
|---|---|---|---|---|
| Example 5 | green tea extract powder 70% | microcrystalline cellulose 30% | HPMC aqueous solution (2.5%) | 1. active ingredient + diluent 2. adding binder (or wetting agent) |
| Example 6 | green tea extract powder 70% | microcrystalline cellulose 30% | HPMC aqueous solution (2.5%) | 1. diluent + binder (or wetting agent) 2. adding active ingredient |
| Example 7 | green tea extract active pellet[a] 70% | microcrystalline cellulose 30% | HPMC aqueous solution (2.5%) | 1. diluent + binder (or wetting agent) 2. adding active ingredient |
| Example 8 | green tea extract active pellet[a] 70% | ginger fiber 30% | HPMC aqueous solution (2.5%) | 1. diluent + binder (or wetting agent) 2. adding active ingredient |

[a]the green tea extract active pellet is manufactured by 50% green tea extract powder and 20% ginger fiber In the pre-treated process of Example 5, the active ingredient (green tea extract powder, EGEG content 70%, Mino) was mixed with 150 g microcrystalline cellulose, and then 150 ml (HPMC aqueous solution, 2.5%) binder was added therein.

As to the pre-treated process of example 6, 150 g microcrystalline cellulose was added with 150 ml binder (HPMC aqueous solution, 2.5%) and hold for 30 minutes; 350 g green tea extract powder (EGEG content 70%, Mino) having high viscosity was then added therein.

In Example 7, green tea extract pellets were prepared, and pre-treated process was then performed. First, the diluent, the binder and 150 ml water were mixed and then hold for 30 minutes. Next, the active ingredient having high viscosity was added and extruded and spheronized by using a 0.4 mm orifice plate (ratio of holes is about 1%). Next, the particles are dried to form pellets (EGEG content being about 49%) with a diameter of about 0.4 mm. Subsequently, 150 g microcrystalline cellulose and 150 ml HPMC aqueous solution (2.5%) were mixed, and 350 g pellets ere added therein.

In Example 8, green tea extract pellets were prepared, and pre-treated process was then performed. First, the diluent, the binder and 150 ml water were mixed and then hold for 30 minutes. Subsequently, the active ingredient having high viscosity was added, and extruded and spheronized by using a 0.4 mm orifice plate (ratio of holes is about 1%). Next, the particles were dried to form pellets (EGEG content is about 49%) with a diameter of about 0.4 mm. Next, 150 g microcrystalline cellulose and 150 ml HPMC aqueous solution (2.5%) were mixed, and 350 g pellets were added therein.

After the pre-treated process, the above products were extruded and spheronized in sequence. The pellets after the spheronization process were dried at 60° C. for 3 hours.

In Example 5, the elongated particles were extruded by a single-screw extruder with a 1.0 mm orifice plate, spheronized by using a centrifugal turntable with 800 rpm for 30 seconds and were dried out. The pellets had a shape of long rather than ball-like, and of poor uniformity in size. Since the mixture formed after pre-treated process had high viscosity, it can be extruded but rather than be spheronized to form a ball-like shape.

In Example 6, the elongated particles were extruded by a single-screw extruder with a 1.0 mm orifice plate, and then spheronized by using a centrifugal turntable at 800 rpm for 30 seconds and then were dried. The pellets are ball-like in shape and showed better size uniformity compared to the pellets of Example 5. However, the yield (size in a range of 0.9 mm to 1.0 mm) was lower than 70% since the mixture formed by pre-treated process possessed suitable viscosity. Therefore, although Example 6 was the same as Example 5 in composition, the process of Example 6 can help reduce the viscosity.

In Example 7, the elongated particles were extruded by a single-screw extruder with a 1.0 mm orifice plate, spheronized by using a centrifugal turntable at 800 rpm for 30 seconds and then dried. The pellets were ball-like in shape and have better size uniformity compared to pellets of Example 6. However, the yield (size in a range of 0.9 mm to 1.0 mm) was higher than 90%, and the characteristics of the pellets were similar to typical pellets since the mixture formed by pre-treated process had suitable viscosity. Further, adding water to the pellets having the green tea extracts would not rapidly increase viscosity.

In Example 8, the elongated particles were extruded by a single-screw extruder with a 1.0 mm orifice plate, and then spheronized by using a centrifugal turntable at 800 rpm for 30 seconds and dried. The pellets were ball-like in shape and have similar size uniformity to pellets of Example 7. The yield (size in a range of 0.9 mm to 1.0 mm) was higher than 90%, and the characteristics of the pellets were similar to typical pellets since the mixture formed by pre-treated process had suitable viscosity. Further, adding water to the pellets having the green tea extracts would not rapidly increase viscosity. In addition, the ginger fiber had the same function as microcrystalline cellulose.

As mentioned above, by various processes, the substances having inadequate viscosity can be processed to form active pellets without chemical additives and change the property for further processing; that is, the active pellets above and other substances (e.g. natural diluent or water) are mixed without becoming a high-viscous substance. Therefore, the active pellets can be widely applied to manufacture a variety of formulations without using any chemical additives so as to significantly reduce hazards to a human body.

Although the present disclosure has been described in considerable detail with reference to certain embodiments thereof, other embodiments are possible. Therefore, the spirit and scope of the appended claims should not be limited to the description of the embodiments contained herein.

It will be apparent to those ordinarily skilled in the art that various modifications and variations may be made to the structure of the present disclosure without departing from the scope or spirit of the disclosure. In view of the foregoing, it is intended that the present disclosure cover modifications and variations thereof provided they fall within the scope of the following claims.

What is claimed is:

1. An active pellet free of chemical additives, comprising:
   a body comprising 50 to 85 wt % of an active ingredient and 15 to 50 wt % of an natural diluent, which is a material selected from the group consisting of ginger fiber, tumeric, pepper, garlic, astragulas, bamboo leaves, mangosteen shell, rambutan peel, yam, tea, orange peel, sweet potato peel, potato peel, dried bagasse powder and a combination thereof; and
   a plurality of interspaces in the body.

2. The active pellet of claim 1, wherein the natural diluent comprises the ginger fiber.

* * * * *